United States Patent
Papavero et al.

[11] Patent Number: 5,755,798
[45] Date of Patent: May 26, 1998

[54] INTERVERTEBRAL IMPLANT

[75] Inventors: Luca Papavero, Hamburg; Curt Kranz; Gerd Steur, both of Berlin, all of Germany

[73] Assignee: Artos Medizinische Produkte GmbH, Berlin, Germany

[21] Appl. No.: 736,802

[22] Filed: Oct. 25, 1996

[30] Foreign Application Priority Data

Oct. 26, 1995 [DE] Germany .................. 195 41 114.5

[51] Int. Cl.$^6$ .................................................. A61F 2/44
[52] U.S. Cl. ................ 623/17; 623/18; 606/61; 606/69; 606/70
[58] Field of Search .................. 623/17, 18, 20; 606/60, 61, 69, 70, 71, 53

[56] References Cited

U.S. PATENT DOCUMENTS

| | | | |
|---|---|---|---|
| 5,556,431 | 9/1996 | Buttner-Janz | 623/17 |
| 5,609,635 | 3/1997 | Michelson | 623/17 |
| 5,658,335 | 8/1997 | Allen | 623/17 |

FOREIGN PATENT DOCUMENTS 0179695  4/1986  European Pat. Off. .
WO94/05235  3/1994  WIPO .

OTHER PUBLICATIONS

Griffith et al. SPINE, vol. 19, No. 16, pp. 1842–1849, (1994).

*Primary Examiner*—Paul B. Prebilic
*Attorney, Agent, or Firm*—Spencer & Frank

[57] ABSTRACT

An intervertebral implant for insertion between adjacent vertebrae. The implant includes a spacer having two end faces and defining a continuous hollow channel therein configured to receive natural bone substance; and flanges disposed on respective end faces of the spacer and extending in each respective end plane thereof for connection to the adjacent vertebrae. Each flange projects laterally beyond the spacer at at least one region of the spacer for reducing surface pressure exerted by the spacer on the vertebrae, at least one flange defining an aperture therein within a region of the hollow channel, the aperture being configured to receive a substrate therein for supporting the natural bone substance, the flanges further defining at least one perforation within a region thereof projecting laterally beyond the spacer through which the natural bone substance may grow along an outside region of the spacer.

18 Claims, 2 Drawing Sheets

5,755,798

INTERVERTEBRAL IMPLANT

FIELD OF THE INVENTION

The invention relates to an intervertebral implant.

BACKGROUND OF THE INVENTION

WO 94/05235 discloses an intervertebral implant which makes it possible to replace, spatially, a natural disc and secure the vertebrae adjacent to said disc in a fixed position relative to one another.

Stabilisation of this kind is important in the case of a damaged disc, since compression of the intervertebral space or a relative lateral displacement of the vertebrae with respect to one another, could lead to damage of the spinal cord and roots resulting in neurologic deficits of the patient.

The known intervertebral implant has a substantially rigid spacer which is inserted surgically between two vertebrae to replace the natural disc, thereby preventing a height reduction of the intervertebral space.

For securing the spacer, the surfaces thereof which are in engagement with the vertebrae are provided with a profiled surface. This increases the friction between the vertebrae and the spacer, thus making a displacement of the spacer between the vertebrae less likely.

The known intervertebral implant also has a hollow channel extending from the top downwards which enables the natural bone material to grow into the spacer and hence the two adjacent vertebrae to grow together.

The disadvantage of this known intervertebral implant, however, is that the spacer subjects the adjacent vertebrae to great mechanical strain. Thus, when the spine of the person carrying the prosthesis is subjected to stress, relatively high mechanical tensions are produced at the point of connection between the spacer and the vertebrae.

Furthermore, there is the problem that the bony ingrowth from the two vertebrae develops relatively slowly because of the hollow channel.

SUMMARY OF THE INVENTION

The invention, therefore, has the object of providing an intervertebral implant of the above kind which subjects the vertebrae to the least possible mechanical strain and enables a rapid growing together of the vertebrae.

This object is achieved by providing an intervertebral implant for insertion between adjacent vertebrae comprising: a spacer having two end faces and defining a continuous hollow channel therein adapted to receive natural bone substance; and flanges disposed on respective end faces of the spacer and extending in each respective end plane thereof for connection to the adjacent vertebrae. Each flange projects laterally beyond the spacer at at least one region of the spacer for reducing surface pressure exerted by the spacer on the vertebrae, at least one flange defining an aperture therein within a region of the hollow channel, the aperture being adapted to receive a substrate therein for supporting the natural bone substance, the flanges further defining at least one perforation within a region thereof projecting laterally beyond the spacer through which the natural bone substance may grow.

The invention proposes that the contact surface between the spacer and adjacent vertebrae in an intervertebral implant be large enough to reduce the surface pressure exerted by the spacer onto the vertebrae and that the hollow channel be formed in such a way that it is possible to introduce a substrate member into it which promotes bone growth.

According to the invention, a plate is provided on each end face of the spacer, which supports the two adjacent vertebrae in the implanted state. These plates may either be moulded or fixedly secured to the spacer, for example by welding. The two plates each have an opening within the region of the hollow channel.

On the one hand, this makes it possible for natural bone substance of the two vertebrae to grow into the hollow channel and for the two vertebrae to grow together to form a unit.

On the other hand, a scaffold which serves as a support for the natural bone substance is inserted into the hollow channel. Its outer dimensions are adapted to the inner dimensions of the hollow channel, thus substantially filling it. This substrate consists, in particular, of a porous material which is adapted to the natural bone substance in such a way that the latter grows into it, thereby providing a mechanically firm connection. The measures of the invention ensure, here, that the elasticity and stability characteristics of the implant are adapted to those of the surrounding bone region, so that the implant, when grown in, follows the micro movements of the bone region in an isoelastic manner without any significant differences in length occurring within the region of adaptation, which might fracture or tear the growth connection. Here, the other measures described below are also of special importance. By means of a corresponding profiling which absorbs transverse shearing forces, a firm securing of the implant which is placed into its intended position after surgery is ensured.

The substrate is not very bulky either so that, on the one hand, a relatively large amount of bone mass is able to grow into it, thus forming a stable bone connection between the two vertebrae. On the other hand, though it is low in bulk, the substrate material may completely fill the hollow channel and thus form a good support for the natural bone mass.

The outer cross-section of the substrate is preferably adapted to the inner or internal cross-section of the hollow channel in such a way that there is play between the hollow channel in a plane perpendicular to a longitudinal axis of the spacer and the substrate member. This means, on the one hand, that the substrate may be pushed into the hollow channel without great effort. On the other hand, the substrate guided by the hollow channel and is therefore positioned in the spacer, as specified.

Preferably, the substrate is prefabricated and adapted to the spacer. This obviates the relatively expensive insertion and adaptation of the carrier material upon implantation, which is normally necessary when it is not prefabricated. This saves time during the implantation, on the one hand, which is an advantage and in the interest of patient care. On the other hand, a prefabricated substrate ensures a uniform quality of the carrier material with a uniform porosity over the entire volume of the hollow channel, which contributes to a quick growing together of the two vertebrae.

In an advantageous variant of the invention which is, itself, of patentable significance, the substrate is largely made of a ceramics material baked from bovine spongiosa. This ensures a high biocompatibility, on the one hand, and makes it possible for the bone to grow more quickly into the vertebral space, on the other hand.

In another variant of the invention which is, itself of patentable significance, the substrate member is made of a material which promotes bone growth. This also accelerates the formation of a natural bone connection between the two vertebrae.

According to the invention, the area of the plates is larger than the cross-sectional contact surface area of the spacer.

The contact surface area of each plate represents that surface area of the plate adapted to be positioned immediately adjacent a vertebra. The plates, therefore, project laterally from the spacer.

This reduces the mechanical stresses suffered by the vertebrae as, in the event of an axial load on the spinal column, the force transferred from the spacer to the vertebrae is distributed over a larger area because of the plates.

Though the surface pressure acting upon the vertebrae is reduced due to the large area of the plates arranged on the top and bottom of the spacer, these plates basically prevent the adjacent vertebrae from growing together, since they stop the growth of the natural bone material.

According to the invention, therefore, the outside of the plates have at least one aperture through which the bone substance may grow along the outside of the spacer. Thus, after implantation, the natural bone substance, starting from the adjacent vertebrae, grows, on the one hand, through the hollow channel in the spacer and, on the other hand, through the apertures in the places arranged on the end faces of the spacer, along the outside of the spacer into the interior of the intervertebral space.

Thus, the intervertebral implant according to the invention combines the advantages of a relatively thin spacer adapted in its dimensions in the original disc with the advantages of large contact faces. A thin spacer only fills a relatively small volume of the intervertebral space so that a large amount of natural bone substance is able to grow into the intervertebral space and form a natural bone connection between the two adjacent vertebrae. The mechanical stresses of the vertebrae are also relatively small because of the large contact areas between the vertebrae and the intervertebral implant.

On the one hand, the intervertebral implant must be sufficiently rigid and firm in order to largely prevent movement of the vertebrae relative to one another, when the spinal column is subjected to stress during the growing together of the two adjacent vertebrae, which would be impeded by such relative movement.

On the other hand, the intervertebral implant must not be substantially more rigid than the natural bone substance This is due to the fact that the stresses after the growing together of the two adjacent vertebrae must be absorbed both by the intervertebral implant and by the natural bone substance grown into the intervertebral space. This, however, would not be possible if the intervertebral implant were significantly more rigid than the natural bone substance since the stresses would be almost exclusively absorbed by the intervertebral implant.

As explained, the spacer has, preferably, a similar resilience to that of natural bone substance. In a preferred embodiment, perforations are provided laterally in the wall of the spacer which reduce the rigidity of the spacer and thus increase the resilience of the intervertebral implant.

In an advantageous further development of the invention, the two plates are in parallel arrangement, relative to one another, for connection to the adjacent vertebrae.

However, the natural spinal column is not entirely straight but curved and it is therefore desirable in many cases, that the intervertebral implant is curved at the site of implantation, to conform with the natural curvature of the spinal column. In an advantageous variant of the invention, the two plates are, therefore, at a slight angle, relative to one another, to correspond to the natural curvature of the spinal column.

For the natural bone material to grow into the intervertebral implant, it is important that the hollow channel is freely accessible. In an advantageous further variant of the invention, the spacer is constructed as a meshed cage. This enables a largely undisturbed circulation of endogenic substances in the intervertebral space thereby allowing rapid bone growth.

In order to replace the disc, the intervertebral implant according to the invention is placed surgically between two vertebrae, thus preventing compression of the intervertebral space. In this context, it is extremely important that the intervertebral implant is secured between the two vertebrae, since a displacement of the implant could lead to damage to the nerves by the implant itself, or to a compression of the intervertebral space which would also result in damaged nerves.

Therefore, in another advantageous further development of the invention which, itself, is of patentable significance, the surface of the plates is provided with a profile on the side facing the vertebrae This increases the friction between the intervertebral implant and the vertebrae and thus makes a displacement of the implant less likely.

In a preferred embodiment of this variant, this surface profile consists substantially of circular concentric grooves, relative to the longitudinal axis of the hollow channel. The elevations between these grooves are pressed into the vertebrae after implantation as a result of the stresses acting between the vertebrae, thereby securing the intervertebral implant between the two vertebrae. The implant is secured, with respect to the shearing stresses in the transverse direction, preventing lateral pressing out of the implant from the intervertebral space Here, the greater load-carrying capacity with respect to shearing stresses, which results from the profiled surfaces, is advantageously independent of the direction of the shearing stresses, since the concentric grooves or elevations of the profile surfaces are arranged so as to encircle the longitudinal axis of the hollow channel and thus do not have a preferred direction.

In the above variants of the invention, the intervertebral implant is preferably frictionally connected with the adjacent vertebrae, as a result of the friction, acting between the vertebrae and the profiled plate surface. In such a frictional connection, however, a displacement of the vertical implant cannot be ruled out with certainty. This is of particular disadvantage during the period when the two adjacent vertebrae grow together as the implant will then have to bear the mechanical load on its own. Furthermore, a movement of the intervertebral implant in the intervertebral space impedes the growing together of the two adjacent vertebrae.

In a further development of the invention which, itself, is of patentable significance, anchorage members are therefore provided which frictionally connect the two plates with the adjacent vertebrae. In a preferred embodiment, bone screws are provided which are inserted into the plates through bores and screwed into the vertebrae.

Such a frictional connection enables the implant to absorb any bending stresses to which the spinal column is subjected.

BRIEF DESCRIPTION OF THE DRAWINGS

Further advantageous developments of the invention are hereinafter described in more detail with reference to the drawings, which illustrate a preferred embodiment of the invention. Shown are.

DETAILED DESCRIPTION OF THE INVENTION

Figure 1:
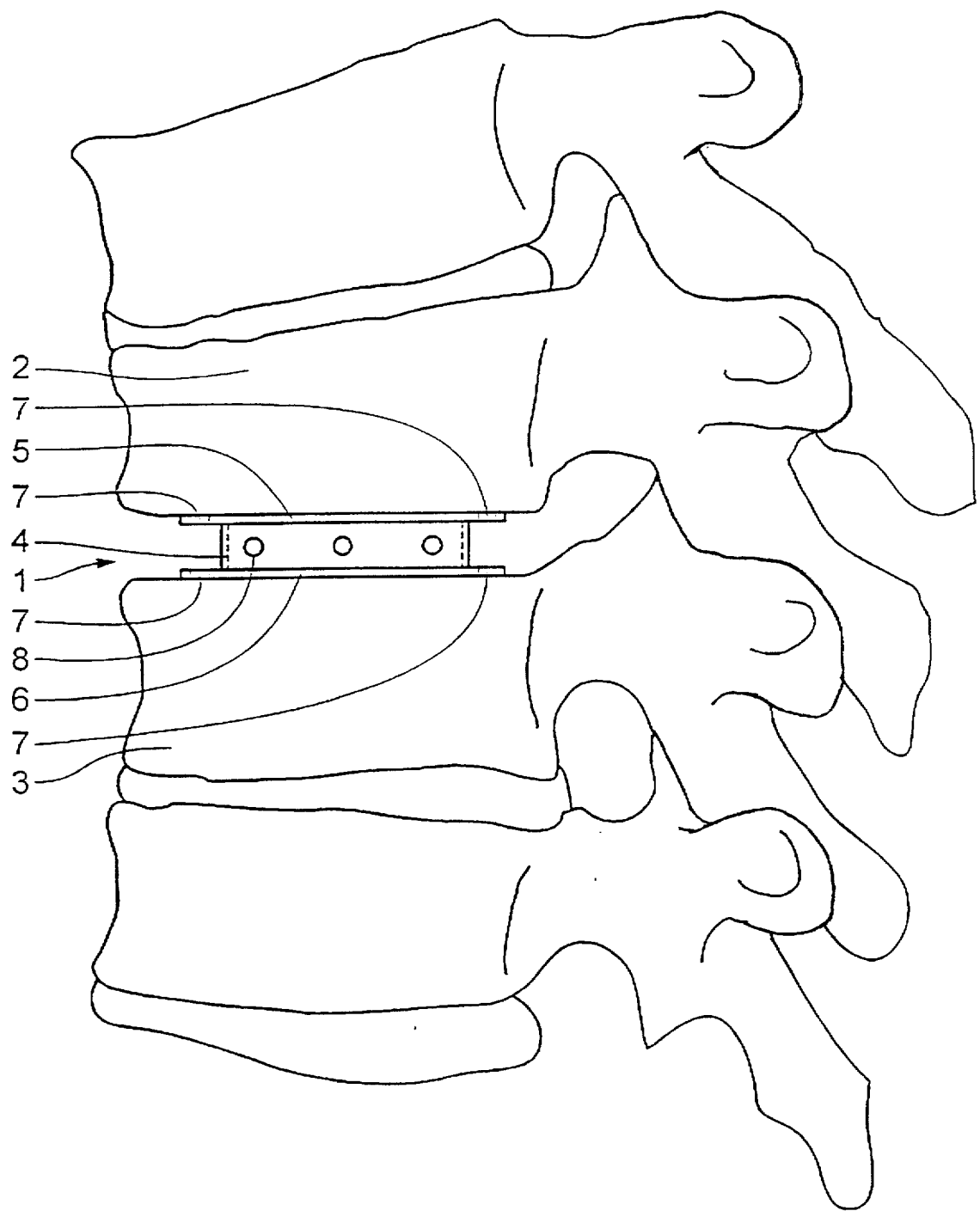
FIG. 1, an intervertebral implant in the implanted state, in a side-elevational view, as a preferred embodiment of the invention, FIG. 2a, the intervertebral implant shown in FIG. 1, in a perspective representation, and FIG. 2b, the substrate member of the intervertebral implant shown in FIGS. 1 and 2a, in a perspective representation.

The side-elevational representation shown in FIG. 1, shows, on the one hand, the construction of the intervertebral implant 1 and, on the other hand, the arrangement of the intervertebral implant 1 between two vertebrae 2, 3 for replacing a natural disc.

The intervertebral implant 1 shown mainly comprises a cylindrical spacer 4 with an outer diameter of about 14 mm and a height of 5 mm. This spacer has, in replacement of the natural disc, the object of securing the two adjacent vertebrae 2, 3 at a fixed spacing relative to one another, in order to prevent a compression of the intervertebral space which would make nerve damage likely.

In order to connect the intervertebral implant 1 with the vertebrae 2, 3, a rectangular plate 5, 6 of 17 mm in length and 15 mm in width is moulded to the top and bottom of the spacer 4. As the area of the contact surface plates 5, 6 is larger than the cross-sectional area of spacer 4 in a plane perpendicular to a longitudinal axis of the spacer, the surface pressure acting upon the vertebrae 2, 3 at the region of connection in the event of the implanted intervertebral implant 1 being subjected to stress is reduced. This means there is less strain on the vertebrae 2, 3.

The two plates 5, 6 are in a parallel arrangement here so that the two vertebrae 2, 3 next to the disc to be replaced are interconnected without curvature.

The spacer 4 has a hollow cylindrical channel, which is continuous from the top to the bottom and enables a growing-in of natural bone material thus providing a natural bone connection between the two adjacent vertebrae 2, 3. In the end stage the two adjacent vertebrae 2, 3 then form a firm bone unit so that mechanical stresses, to which the vertical column is subjected, are absorbed partly by the implant 1 and partly by the natural, bone connection after the two vertebrae 2, 3 have grown together.

The plates 5, 6 have at their centre a circular aperture which encompasses the entire cross-section of the hollow channel in a plane perpendicular to a longitudinal axis of the spacer so that they make it possible for natural bone material to grow into the spacer 4.

Furthermore, several perforations 7 are provided in each corner of the outside of plates 5, 6 which make it possible for natural bone material to grow through them along the outside of the spacer 4.

The natural bone substance thus grows from the two adjacent vertebrae 2, 3 into the intervertebral space through the hollow channel in the spacer 4, on the one hand, and through the perforation 7 in the plates 5, 6 along the outside of the spacer 4, on the other hand. The growing-together of the two adjacent vertebrae 2, 3 is therefore only slightly impeded by the interposed plates 5, 6.

The side wall of spacer 4 also has circular perforations 8 of about 3 mm in diameter which allow free circulation of body fluid in the intervertebral space. This also contributes to a rapid growing together of the two adjacent vertebrae 2, 3.

These perforations 8 moreover increase the resilience of spacer 4. This is of advantage since the mechanical stresses are intended to be absorbed jointly by the intervertebral implant 1 and the natural bone substance grown into it, after the two adjacent vertebrae have grown together.

Figure 2A:
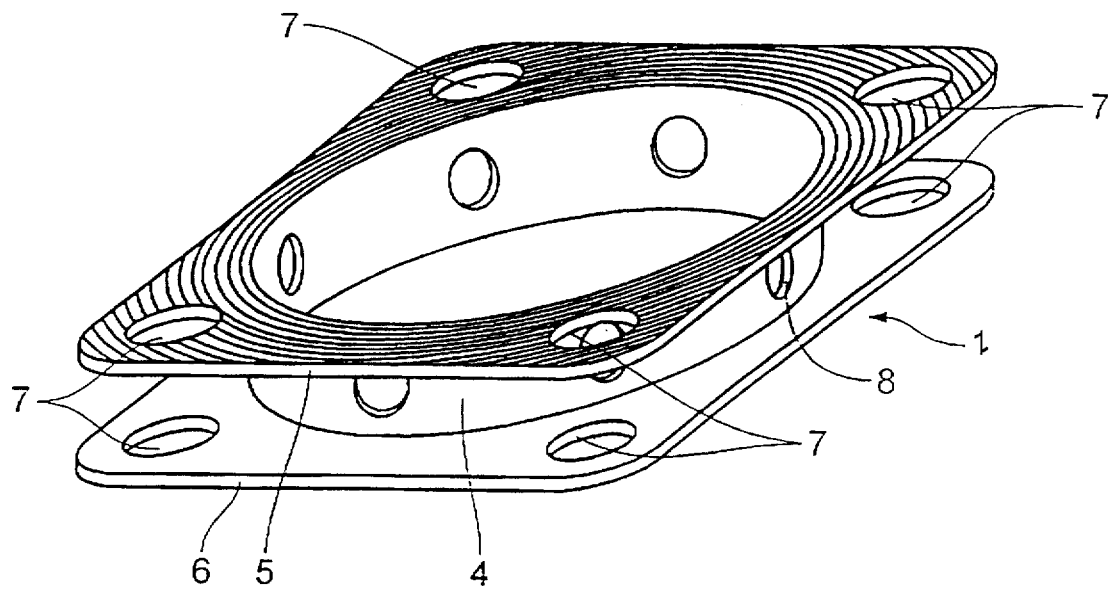

The perspective representation of the implant 1 illustrated in FIG. 2a also shows that plates 5, 6 have a surface profile in the form of circular grooves, at the side facing the vertebrae.

The elevations between these grooves are pressed into the vertebrae after implantation because of the stresses acting between the vertebrae, thereby preventing a lateral displacement of the intervertebral implant 1. The shearing forces produced at the contact face of intervertebral implant 1 and vertebrae, if the spinal column is subjected to shearing stresses, are thus absorbed by the surface profile which is in engagement with the vertebrae.

FIG. 2a also shows that plates 5, 6 have at their centre a circular aperture which encompasses the entire cross-section of the hollow channel extending through the spacer 4. The cross-section of this hollow channel is uniform along the longitudinal axis thereof. This makes it possible to push a substrate member in the form of a tablet which serves as a support for the natural bone substance, easily into the hollow channel.

The arrangement of perforations 7 is also shown. They are correspondingly arranged in the corners of plates 5, 6 and make it possible for natural bone substance to grow into the intervertebral space at the outside of spacer 4.

Figure 2B:
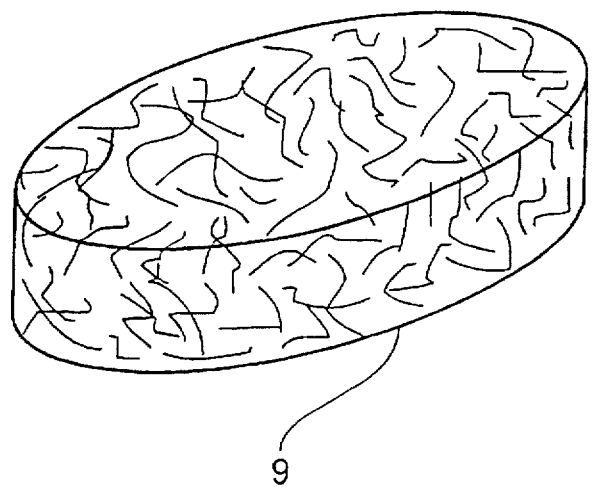

The substrate 9 is shown in detail in FIG. 2b. It is mainly made of a porous ceramic material. Because of its porosity, the actual volume of the inserted piece is relatively low so that, on the one hand, a relatively large amount of natural bone substance can grow into the hollow channel arid, on the other hand, the substrate 9 entirely fills the hollow channel thereby providing a support for the natural bone substance throughout the entire volume of the hollow channel. By using a support for the natural bone substance, instead of a hollow channel, the bone growth is accelerated and a quick growing together of the adjacent vertebrae is achieved.

The substrate 9 largely consists of a ceramics material burnt from bovine spongiosa. This provides, on thee one hand, a high bicompatibility and, on the other hand, affects bone growth in a positive manner. Furthermore, after the ceramics material has been burnt, substances are contained in the substrate material 9 which promote bone growth and further accelerate the growing together of the two vertebrae.

The substrate 9 is of a cylindrical shape so that the intervertebral implant can be pushed into the hollow channel. The cross-section of the substrate is therefore adapted to the cross-section of the hollow channel.

The invention is not restricted in its configuration to the preferred exemplary embodiment specified above Rather, a number of variants which make use of the solution described are conceivable, even in the case of configurations of a fundamentally different type.

We claim:

1. An intervertebral implant for insertion between adjacent vertebrae comprising:

a spacer having two end faces and defining a continuous hollow channel therein adapted to receive natural bone substance;

flanges disposed on respective end faces of the spacer and extending in each respective end plane thereof for connection to the adjacent vertebrae, each flange projecting laterally beyond the spacer at at least one region of the spacer for reducing surface pressure exerted by the spacer on the vertebrae, at least one flange defining an aperture therein within a region of the hollow channel, the aperture being adapted to receive a substrate therein for supporting the natural bone substance, the flanges further defining at least one perforation within a region thereof projecting laterally beyond the spacer for receiving natural bone substance which may grow along an outside region of the spacer.

2. The implant according to claim 1, wherein the spacer has a substantially tubular shape and a substantially constant internal cross-section along a longitudinal direction thereof.

3. The implant according to claim 1, further comprising a substrate disposed in the aperture of the at least one flange.

4. The implant according to claim 3, wherein an internal cross section of the hollow channel is equal to or larger than an outer cross section of the substrate along a longitudinal direction of the spacer.

5. The implant according to claim 1, wherein an internal cross section of the hollow channel along a longitudinal direction of the spacer is substantially circular.

6. The implant according to claim 1, wherein the spacer is substantially rigid.

7. The implant according to claim 1, wherein the spacer has a resilience which largely corresponds to a resilience of the natural bone substance.

8. The implant according to claim 1, wherein the spacer defines at least one perforation facing in a radial direction for increasing a resilience thereof.

9. The implant according to claim 8, wherein the spacer is configured as a meshed cage for allowing the natural bone substance to grow into the cage.

10. The implant according to claim 1, wherein the flanges are substantially parallel to one another or at a slight angle with respect to one another to conform with a natural curvature of a vertebral column.

11. The implant according to claim 1, wherein the implant is made of a titanium or a titanium alloy.

12. The implant according to claim 3, wherein the substrate is made of a porous material.

13. The implant according to claim 3, wherein the substrate is made of a ceramics material burnt from bovine spongiosa.

14. The implant according to claim 3, wherein the substrate contains substances which promote bone growth.

15. The implant according to claim 1, wherein at least one of the flanges defines a surface profile on a side thereon facing a corresponding vertebra.

16. The implant according to claim 15, wherein the surface profile comprises a plurality of circumferentially extending grooves.

17. The implant according to claim 1, further comprising anchorage elements adapted to be fastened to the plates for positively connecting the plates to the vertebrae.

18. The implant according to claim 17, wherein the anchorage elements comprise bone screws.

* * * * *